US010729960B2

(12) United States Patent
Logan

(10) Patent No.: US 10,729,960 B2
(45) Date of Patent: Aug. 4, 2020

(54) SYSTEM AND METHOD FOR IMPROVING BOWLING SHOT PERFORMANCE

(71) Applicant: Kevin Logan, Pawcatuck, CT (US)

(72) Inventor: Kevin Logan, Pawcatuck, CT (US)

(*) Notice: Subject to any disclaimer, the term of this patent is extended or adjusted under 35 U.S.C. 154(b) by 107 days.

(21) Appl. No.: 15/923,706

(22) Filed: Mar. 16, 2018

(65) Prior Publication Data
US 2018/0264337 A1 Sep. 20, 2018

Related U.S. Application Data

(60) Provisional application No. 62/472,800, filed on Mar. 17, 2017.

(51) Int. Cl.
A63B 69/00 (2006.01)
A63B 24/00 (2006.01)
G06K 17/00 (2006.01)
G06F 1/16 (2006.01)
G06F 3/01 (2006.01)
G06K 9/00 (2006.01)
A63B 71/14 (2006.01)
A61B 5/11 (2006.01)
A61B 5/00 (2006.01)

(52) U.S. Cl.
CPC ............ *A63B 69/0046* (2013.01); *A61B 5/11* (2013.01); *A61B 5/1124* (2013.01); *A61B 5/6806* (2013.01); *A63B 24/0006* (2013.01); *A63B 71/148* (2013.01); *G06F 1/163* (2013.01); *G06F 1/1694* (2013.01); *G06F 3/014* (2013.01); *G06K 9/00342* (2013.01); *G06K 17/0022* (2013.01); *A61B 2503/10* (2013.01); *A61B 2562/0219* (2013.01); *A63B 2220/803* (2013.01); *G06F 2200/1637* (2013.01)

(58) Field of Classification Search
CPC .............. A63B 69/0046; A63B 71/148; A63B 24/0006; G06F 1/163; G06K 9/00342
See application file for complete search history.

(56) References Cited

U.S. PATENT DOCUMENTS

| 6,110,052 A  | * | 8/2000  | Sprager  | A63D 5/04  |
|              |   |         |          | 340/323 B  |
| 7,845,225 B2 | * | 12/2010 | Ridenour | A61B 5/225 |
|              |   |         |          | 73/379.02  |
| 9,610,476 B1 | * | 4/2017  | Tran     | A63B 69/38 |
| 9,814,928 B2 | * | 11/2017 | Taylor   | A63B 21/4049 |

(Continued)

Primary Examiner — Chase E Leichliter
(74) Attorney, Agent, or Firm — Ware, Fressola, Maguire & Barber LLP; Brian L. Wamsley, Esq.

(57) ABSTRACT

A system and method for improving bowling shot performance based on bowling shot metrics calculated from the analysis of bowling shot sensor data from the user are disclosed. The system comprises a motion sensor/computer device integrated with a bowling glove, a microcomputer system, wireless data communications coupled to methods for data capture from the sensorized glove, and a mobile electronic device for accessing and displaying a bowler's current and historical performance data using the Internet. The performance metrics include ball revolutions rate at release, ball speed, force, backswing duration, front swing duration and shot tempo. Comparing the current and historical performance data allows the user to adjust his or her bowling swing accordingly.

20 Claims, 19 Drawing Sheets

(56) References Cited

U.S. PATENT DOCUMENTS

| | | | |
|---|---|---|---|
| 2008/0287204 A1* | 11/2008 | Stremmel | A63D 5/04 |
| | | | 473/58 |
| 2013/0106603 A1* | 5/2013 | Weast | G06F 1/163 |
| | | | 340/539.11 |
| 2016/0217325 A1* | 7/2016 | Bose | G11B 27/17 |
| 2017/0039882 A1* | 2/2017 | Hashimoto | A61B 5/1127 |
| 2018/0078820 A1* | 3/2018 | Bundock | G01P 3/66 |
| 2018/0114460 A1* | 4/2018 | Rivera, Jr. | G09B 19/0038 |

* cited by examiner

SYSTEM AND METHOD FOR IMPROVING BOWLING SHOT PERFORMANCE

RELATED APPLICATIONS

This application claims priority of U.S. Provisional Application No. 62/472,800, filed Mar. 17, 2017, which is specifically incorporated herein by reference in its entirety.

FIELD OF THE INVENTION

The present invention relates to a data-driven integrative system and method for improving bowling shot performance. Specifically, a system and method for improving bowling shot performance by adjusting bowling shot parameters based on a comparison of bowling shot metrics data obtained by previously targeted shots, is described. The method comprises the steps of initiating a bowling shot application on a mobile device, taking bowling shots in either practice or a game, obtaining bowling shot sensor data, computing bowling shot metrics from the sensor data, storing the bowling shot metrics for specific successful bowling shots, displaying the bowling shot metrics on the mobile device, comparing the bowling shot metrics for a current bowling shot with the stored metrics of successful shots and adjusting subsequent bowling shots based on the comparison.

Embodiments of the present invention related to methods and systems for estimating motion parameters and recognizing and quantifying certain activities. More particularly, various embodiments of the invention provide methods and systems operable to estimate specific sports and athletic motion parameters utilizing 3-axis acceleration and 3-axis gyroscope measurements coupled with a wearable computing platform and mobile display devices.

BACKGROUND OF THE INVENTION

Motion parameters, such as acceleration, angular velocity, and a variety of derivative performance metrics, may be utilized in the training and evaluation of athletes, the rehabilitation of injured human patients, and in various recreational activities, including but not limited to both professional and nonprofessional sports. In many sports, such as bowling, tennis, golf, baseball, cricket, table tennis, badminton, basketball and soccer, athletic motions may be decomposed into a series of specific activities, the beginning and end of which can be segmented by specific detectable events. For example, in bowling detectable events include the beginning of the backswing, the end of the backswing or equivalently the beginning of the forward swing, and the end of the forward swing or equivalently ball release from the hand. Using wearable motion sensors integrated into a convenient form factor, motion data can be acquired during play and input into activity recognition algorithms that automatically segment the data into activities, calculate performance metrics on the activity segments, and provide the user/athlete with measurable feedback that will help them improve performance and become more consistent over time.

While the goal of this invention is to provide a system and method by which motion parameters for a bowling shot may be measured, analyzed and compared, resulting in an improvement in a bowler's performance when such comparative information is applied to subsequent bowling shots, it is anticipated that the system and method are applicable not only to a wide range of sports where motion parameters are critical, but also in other areas where it would be beneficial to a person to be able to analyze and compare motion parameters to improve physical performance.

SUMMARY OF THE INVENTION

It is therefor an object of the present invention to provide a system and method for measuring physical motion parameters for a bowing shot. It is a further object of this invention to provide a system and method for analyzing bowling shot motion parameters and calculating bowling shot metrics based on bowling shots that the user targets as ideal shots. Another object of this invention is to provide a visual display of the calculated bowling shot metrics for the user to observe. It is also an object of this invention to provide a method by which a user can improve his or her bowling performance by comparing current bowling shot metrics with previous metrics for targeted shots, and by adjusting subsequent bowling shot metrics to the targeted shot metrics. Lastly, it is an object of this invention to provide a system and method for improving bowling shot performance not provided in the prior art.

Thus the present invention is directed to a method and a bowling shot analyzing system by which a user can improve his or her bowling shot performance, comprising a wearable form factor, such as a bowling glove, wristband, or other bodily attachments or garments, further comprising a microcomputer system having embedded components, such as digital accelerometer sensors, digital gyroscope sensors, and wireless data communications, coupled to methods for body motion data capture, methods for performance metrics calculations, including ball revolutions rate at release, ball speed, force, backswing duration, front swing duration, and shot tempo and other methods for storing and displaying on a mobile device the user's current and historical performance data using the Internet.

Specifically, the system includes a wearable motion sensor device, which could be a wristband, bowling glove, compression sleeve or similar device, which contains an integrated sensor/computing platform, such as digital accelerometer sensors or digital gyroscope sensors. Sensor/computing platform comprises computer programming configured to detect a bowling shot while it is being made and to capture data generated by the bowling shot. The bowling shot sensor data is transmitted via Bluetooth data communications to a mobile device, such as a smart phone or tablet computer. The mobile device contains application software (App) which is configured to receive the transmitted bowling shot sensor data from the wearable device and further transmits the bowling shot sensor data through a cellular or Wi-Fi connection to an Internet-connected Web server computer. The Web server computer receives and stores the transmitted bowling shot sensor data. In some embodiments, the Web server computer calculates bowling shot metrics from the received bowling shot sensor data and communicates the calculated metrics via cellular or Wi-Fi connection back to mobile device for display to the user. In other embodiments, the Web server computer may pass the received bowling shot sensor data to an Internet-connected analytical server computer through an Application Programming Interface (API) call, so that the analytical server computer calculates the bowling shot metrics and communicates the calculated metrics bank to the mobile device through the Web server computer. Once the bowling shot metrics are displayed on the mobile device, the user can determine where there may be deviations in his bowling shot performance based on a comparison of metrics from previously selected bowling shots, and adjust a subsequent bowling shot to conform more closely to stored ideal bowling shot metrics.

BRIEF DESCRIPTION OF THE DRAWINGS

The methods, features, objects, and advantages according to the invention will appear and can be further understood and described in more detail with regard to the accompanying figures. The figures illustrate ways of implementing the present invention and are not to be construed as being limiting to other possible embodiments falling within the scope of the attached claims. The drawings are not necessarily to scale, emphasis instead being placed upon clearly illustrating various embodiments of the invention.

DETAILED DESCRIPTION

Figure 1:
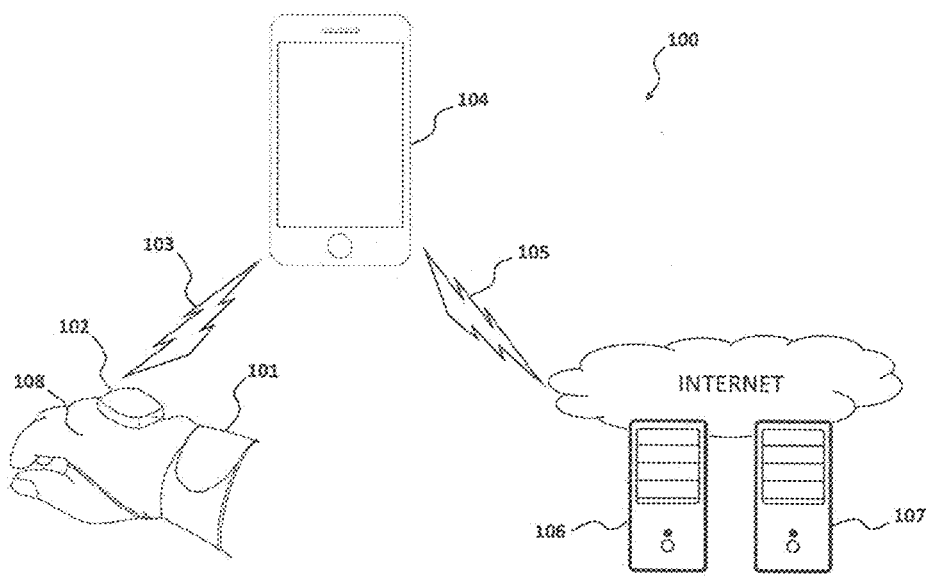
FIG. 1 is a diagram illustrating the overall bowling shot analyzing system.

The preferred embodiments of the present invention will now be described with reference to the FIGS. 1-15 of the drawing. Identical elements in the various figures are designated with the same reference numerals. The following detailed description of various embodiments of the invention illustrates specific embodiments in which the invention can be practiced. The embodiments are intended to describe aspects of the invention in sufficient detail to enable those skilled in the art to practice the invention. Other embodiments can be envisioned, and changes can be made without departing from the scope of the present invention. The following detailed description is, therefore, not to be taken in a limiting sense. The scope of the present invention is defined only by the appended claims, along with the full scope of equivalents to which such claims are entitled.

Referring now to the drawings, FIG. 1 is a diagram illustrating the overall system 100 for analyzing a bowling shot and improving bowling performance. The system includes a wearable motion sensor device 101, which could be a wristband, bowling glove 108, compression sleeve or similar device, which contains an integrated sensor/computing platform 102. Sensor/computing platform 102 may be detachably connected to motion sensor device 101, and comprises computer programming configured to detect a bowling shot while it is being made and to capture data generated by the bowling shot, such as accelerometer and gyroscope data. Sensor/computing platform 102 transmits the bowling shot sensor data via Bluetooth data communications 103 to a mobile device 104, such as a smart phone, tablet computer or similar device. Mobile device 104 contains application software (App) running on mobile device 104, which is configured to receive the transmitted bowling shot sensor data from the wearable device 101. Mobile device 104 is further configured to transmit the bowling shot sensor data through a cellular or Wi-Fi connection 105 to an Internet-connected Web server computer 106. Web server computer 106 is configured to receive and store the transmitted bowling shot sensor data. In some embodiments, Web server computer 106 calculates bowling shot metrics from the received bowling shot sensor data and communicates the calculated metrics via cellular or Wi-Fi connection 105 back to mobile device 104 for display to the user. Web server computer 106 is also configured to store historical user shot data in a database. In other embodiments, Web server computer 106 may pass the received bowling shot sensor data to an Internet-connected analytical server computer 107 through an Application Programming Interface (API) call, wherein analytical server computer 107 calculates bowling shot metrics from the received bowling shot sensor data. Analytical server computer 107 then communicates the calculated metrics back to Web server computer 106, which in turn, communicates the calculated metrics via cellular or Wi-Fi connection 105 to mobile device 104 for display to the user. Once the bowling shot metrics are displayed on mobile device 104, the user can determine where there may be deviations in his bowling shot performance based on a comparison of metrics from previously selected bowling shots. Accordingly, the user can adjust a subsequent bowling shot to conform more closely to stored ideal bowling shot metrics.

Figure 2:
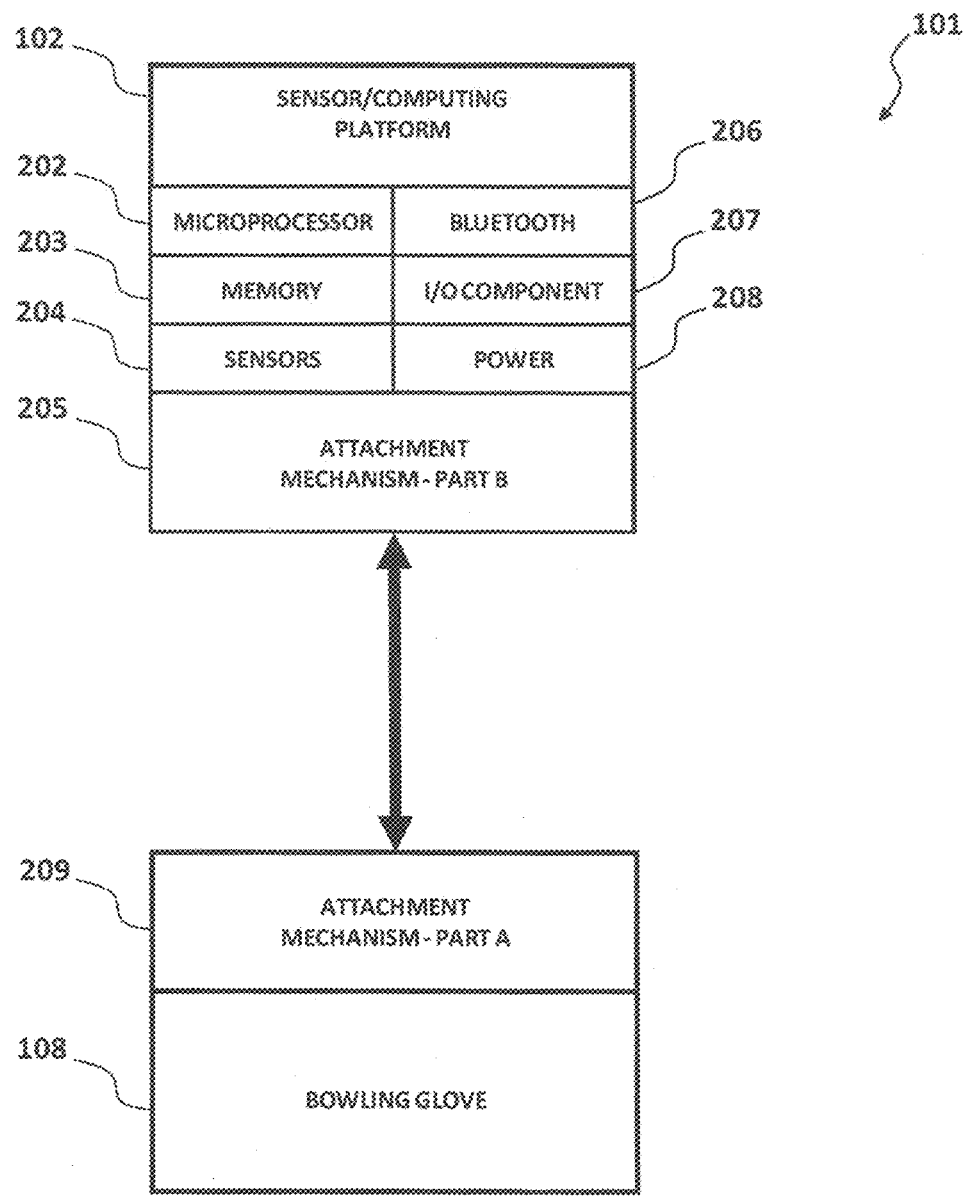
FIG. 2 is a schematic diagram illustrating a wearable motion sensing device in an embodiment of a bowling glove, with an integrated sensor/computing platform and attachment mechanism.

FIG. 2 is a schematic diagram illustrating an embodiment of wearable motion sensor device 101, see also FIG. 1, wherein wearable motion sensor device 101 comprises a bowling glove 108, integrated sensor/computing platform 102, and an attachment mechanism 209, 205. In combination, when worn by a bowler, motion sensor device's 101 shot recognition method stored in microprocessor 202 senses when a bowling shot has occurred and wirelessly transmits bowling shot sensor data via Bluetooth communications 103 to mobile device 104, which can be a smart phone, tablet computer or similar mobile device. Moreover, rather than transmitting bowling shot sensor data continuously, the embedded bowling shot recognition method conserves the power of the included sensor/computing platform 102 by only transmitting sensor data after a shot has been taken by the user, significantly increasing battery life.

Sensor/computing platform 102 comprises a molded plastic housing to fully enclose and protect the internal electronics components. The housing may also include an attachment mechanism 205 to attach sensor/computer platform 102 to bowling glove 108. Attachment mechanism 205, connects directly and securely to a corresponding attachment mechanism 209, that is integral to the bowling glove 108. Examples of attachment mechanisms 205 and 209 are Velcro and snaps.

The internal electronics components of sensor/computing platform 102 comprise a microprocessor 202, a memory 203 containing executable instructions encoding sensor/computing platform's 102 methods and data, motion type sensors 204 that include but are not limited to digital 3-axis accelerometers and digital 3-axis gyroscopes, a Bluetooth communications module 206, Input/Output (I/O) components including a power ON/OFF switch, LED indicator, a micro-USB battery charging connector, and a Power management subsystem 208 that includes a battery and recharging circuitry.

Figure 3A:
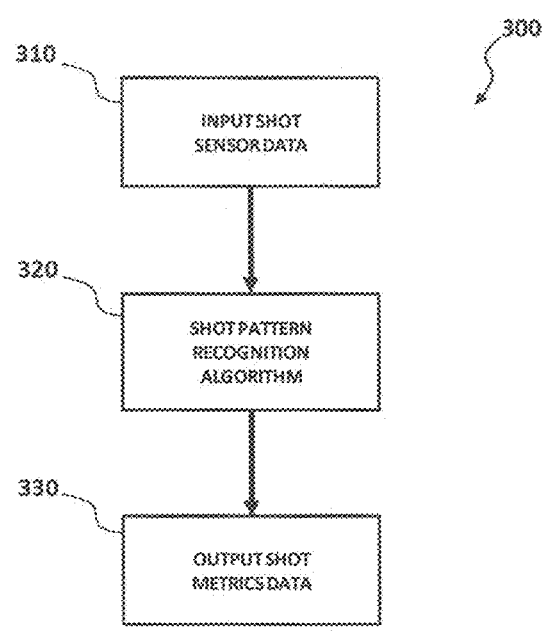
FIG. 3a is a block diagram illustrating an overview of the main analytical server Applications Programming Interface (API)

FIG. 3a summarizes an Applications Programming Interface (API) software module 300 executing on either Web server 106 or analytical server 107 (or both), that computes bowling shot metrics, as follows. API software module 300 receives bowling shot sensor data via its input shot sensor data function 310 in the form of a JSON-formatted data packet sent via the Internet from a remote computer (e.g., Host Server). The data packet contains a date and time stamped recording of a sequential set of sensor data captured from a wearable apparatus, including 3-axis accelerometer and 3-axis gyroscope signals. The data packet also contains numerical values representing a) the data sampling rate in Hz of the wearable apparatus, and b) the weight of ball that was used during the bowling shot.

Input shot sensor data function 310 passes the received sensor data to the shot pattern recognition algorithm function 320, which comprises software that analyzes the 3-axis accelerometer sensor, 3-axis gyroscope sensor, and ball weight data and calculates the following bowling shot metrics:

1) Ball revolution rate at release (RPM)
2) Maximum shot force (KG-M/sec^2)
3) Arm backswing time duration (Seconds)
4) Arm frontswing time duration (Seconds)
5) Bowling shot tempo (non-dimensional)
6) Ball speed at release (MPH)

The results of the shot pattern recognition algorithm function 320 are passed to the output shot metrics data function 330, which comprises software that first prepares a JSON-formatted data packet containing the previously calculated shot metrics, and secondly returns said metrics data to the requesting remote computer (e.g. Host Server) over the Internet using standard Internet data communications protocols.

Figure 3B:
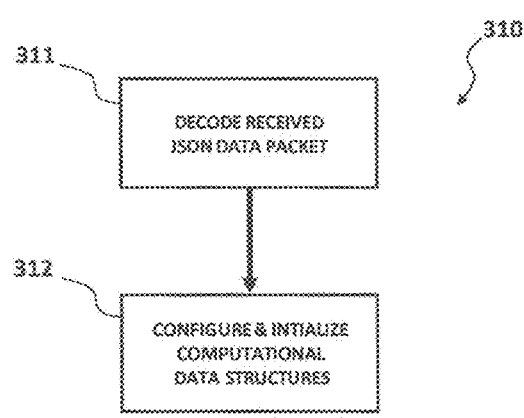
FIG. 3b is a block diagram illustrating the Input Shot Sensor Data function 310.

Similarly, FIG. 3b further defines input shot sensor data function 310 as comprising decode received JSON data packet sub-module 311 and configure & initialize computational data structures sub-module 312. Decode received JSON data packet sub-module 311 converts the received JSON data packet from Internet data communications protocol (e.g., HTTP, TCP/IP, etc.) into internal memory storage values suitable for computer programming. Configure & initialize computational data structures sub-module 312 establishes internal memory data structures comprising all necessary numerical data for executing shot pattern recognition algorithm function 320, and for computing the bowling shot metrics. Key computational data structures comprise arrays for sensor data, including 3-axis accelerometer measurements (X, Y, Z), 3-axis gyroscope measurements (X, Y, Z), as well as the recording timestamp associated with each sensor measurement. In addition, other data structures comprise calculated magnitudes for both accelerometer and gyroscope sensor data, whereby magnitude is calculated as:

$$\text{magnitude} = (X^2 + y^2 + z^2)^{0.5} \tag{1}$$

Each sensor data array represents a time-sequential data series that captures a complete bowling shot of the user, from the initiation of bowler's forward arm swing up to the point of ball release. Time duration of a typical bowling shot ranges from 3-4 seconds and shot pattern recognition algorithm 320 detects key bowling shot event segments from analysis of the sensor data arrays.

Figure 3C:
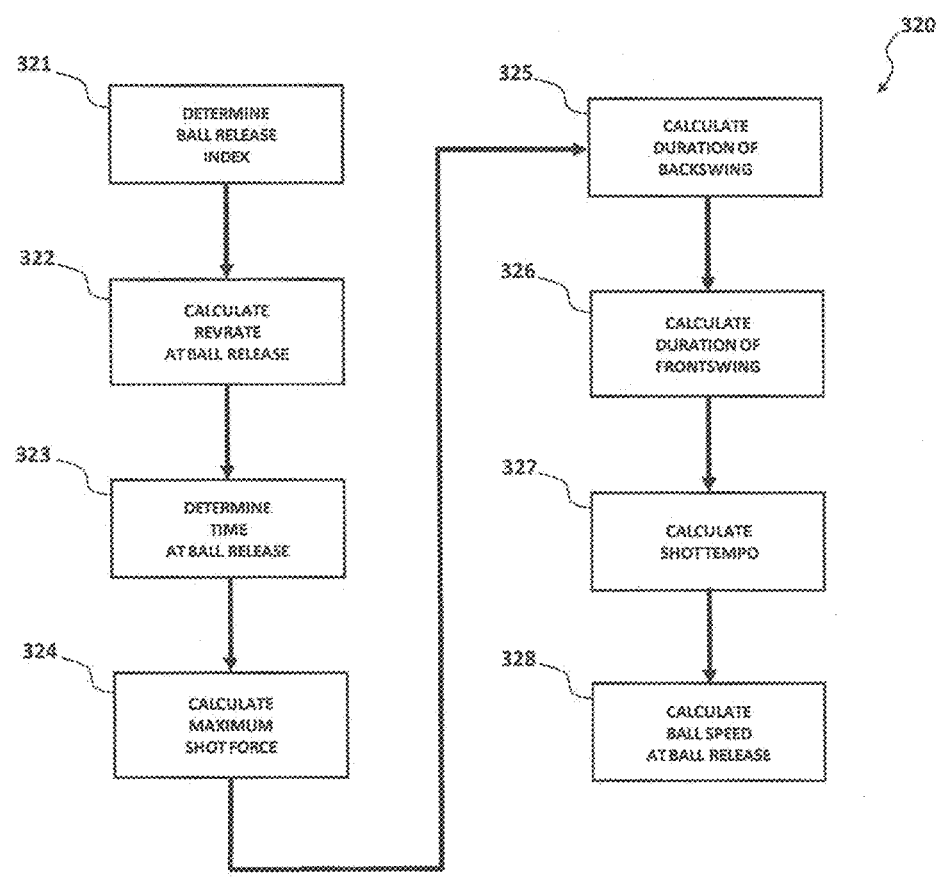
FIG. 3c is a flow diagram illustrating the Shot Pattern Recognition Algorithm 320.

FIG. 3c is a flow diagram for shot pattern recognition algorithm 320, illustrating a series of calculation functions 321-328 that jointly determine the aforementioned bowling shot metrics. Using the magnitude array corresponding to gyroscope sensor measurements from EQ. 1, the determine ball release index function 321 identifies the array index associated with the maximum magnitude value. It is expected that a peak value will occur coincident to the time of ball release. The ball release index thusly determined allows the maximum ball revolutions rate at ball release, herein referenced as RevRate, to be established by the calculate RevRate at ball release function 322. The ball release index thusly determined also similarly allows the time of ball release to be determined by the determine time at ball release function 323. In a similar manner to determine ball release index function 321, the calculate maximum shot force function 324 uses the magnitude array corresponding to accelerometer sensor measurements from EQ. 1 to a) identify an array index associated with the maximum magnitude value, and b) calculate the maximum force from the magnitude array value corresponding to the index and the ball weight provided by input shot sensor data function 310 previously described.

Figure 3D:
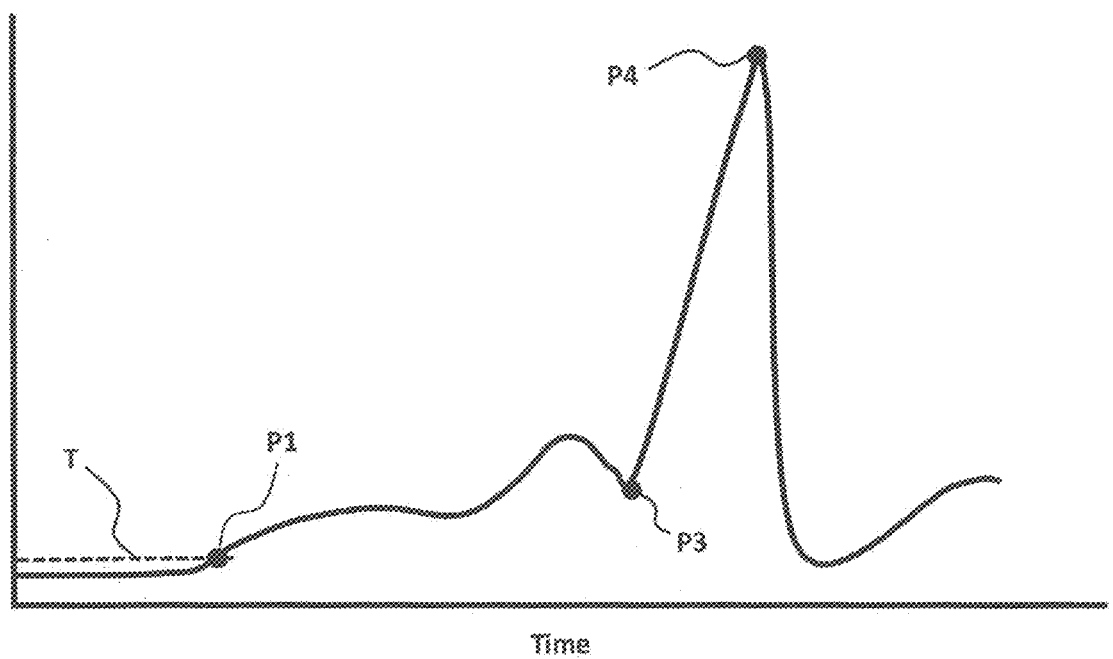
FIG. 3d is a chart illustrating the salient sensor characteristics of a typical bowling shot.

In order to determine the time duration of the backswing and frontswing metrics, the magnitude array calculated from EQ. 1 corresponding the gyroscope sensor measurements is smoothed through a moving average operator to mitigate sensor measurement noise and improve metric precision. As illustrated in FIG. 3d, the key events related to bowling shot metrics include:

1) Start of backswing (point P1)
2) End of backswing=Start of frontswing (point P3)
3) End of Frontswing=Ball release (point P4)

Considering that the time evolution from the Start of backswing event (point P1) to the Ball release event (P4) for most bowlers is in the order of 2-3 seconds, there are alternative methods for bowling shot event recognition. In one embodiment, the calculate duration of backswing function 325 determines the duration of the bowler's backswing as the time difference between points P1 and P3 as illustrated in FIG. 3d, where the chart represents a magnitude versus time plot for a typical bowling shot preceding the ball release at point P4.

Referring to FIG. 3d, in one embodiment point P1 is determined through a thresholding function within a predefined search window on the gyroscope magnitude array. As previously described, determine ball release index function 321 provides a ball release index that allows the time of ball release to be determined by determine time at ball release function 323, herein referred to and illustrated in FIG. 3d as point P4. Starting at point P4 and working backwards in time, a search window for recognizing point P1 is established under the assumption that a typical bowler's shot takes X seconds from start to finish, whereby X may be assigned by either a suitable population average or by a specific bowler's learned value via some calibration function. In either case, a Start Time for a time-based window for searching the gyroscope magnitude array can be established as:

$$\text{Start Time} = \text{time}(P4) - X \quad (2)$$

Through suitable determination of the parameter X, the point P1 can reliably be determined by a method that a) searches the smoothed magnitude data array from the Start Time to time(P4), where said magnitude data increases from a near-zero value at the start of bowler arm swing and subsequently follows the known motion pattern as depicted in FIG. 3d, and b) applies a simple thresholding function on magnitude values within the search time window. In some embodiments of the method, the magnitude threshold, illustrated in FIG. 3d at parameter T, may be assigned a value of approximately 5 degrees per second, although other values may also provide similar accuracy for the determination of point P1 in time.

Also referring to FIG. 3d, the End of backswing (Start of frontswing) event is shown as point P3 on the time scale. In one embodiment, a method for recognizing point P3 is to establish a search window who's lower boundary is approximately one second preceding the point of ball release (P4) and, while searching in a backward direction from point P4, determine when the value of the first derivative of magnitude has a zero or negative value. This zero-derivative point (P3) represents the End of backswing event wherein the bowler's arm changes from a backward direction to a forward direction. Having determined the time values associated with the Start of backswing (point P1) and the End of backswing (point P3), the backswing time duration is calculated as:

$$\text{Backswing Duration} = \text{time}(P3) - \text{time}(P1) \quad (3)$$

Similarly, the calculate duration of frontswing function 326 determines the duration of the bowler's frontswing as the time difference between points P3 and P4 as illustrated in FIG. 3d. More specifically:

$$\text{Frontswing Duration} = \text{time}(P4) - \text{time}(P3) \quad (4)$$

The calculate shot tempo function 327 calculates the metric of Shot Tempo as the numerical ratio of Backswing Duration to Frontswing Duration as:

$$\text{Shot Tempo} = \text{Backswing Duration} \div \text{Frontswing Duration} \quad (5)$$

The calculate ball speed at ball release function 328 calculates the metric of Ball Speed at Release as the numerical integral of the measured acceleration magnitude near the release time as:

$$\text{speed} = \frac{1}{n} \int_{t=a}^{b} M_t \Delta t \quad (6)$$

where
$M_t$=magnitude of acceleration,
a=time(P4−n),
b=time(P4),
n=number of time samples for averaging.

Figure 3E:
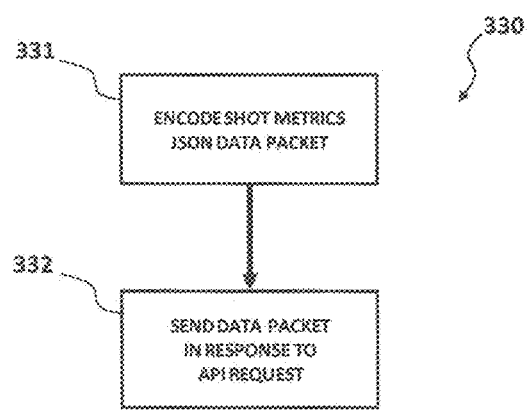
FIG. 3e is a block diagram illustrating the Output Shot Metrics Data function 330.

FIG. 3e illustrates the output shot sensor data function 330 as comprising an encode shot metrics JSON data packet sub-module 331 and a send data packet in response to API request sub-module 332. Encode shot metrics JSON data packet sub-module 311 formats the bowling shot metrics calculated by shot pattern recognition algorithm function 320 into a JSON data packet for transmission. Send data packet in response to API request sub-module 332 executes an HTTP response containing the JSON-formatted bowling shot metrics data to address issuing the API request for data.

Figure 4:
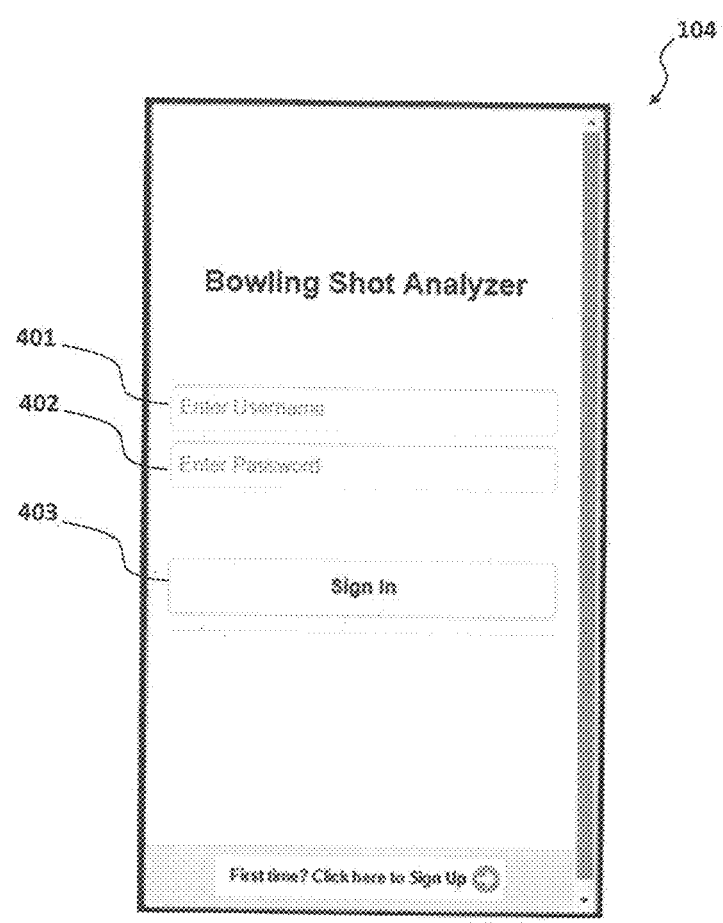
FIG. 4 shows the "log on" screen for the application running on mobile device 104.

In order to store and retrieve bowling shot sensor data and performance metrics data, the user is first required to log on to the bowling shot application on mobile device 104. FIG. 4 shows the log on screen of the application running on the mobile device 104, which allows the user to input his Username 401 and Password 402. The user may click the Sign In button 403 to connect to the backend Web Server 106. The user's log on credentials are posted to a validation program running on the Web Server 106, which validates the user by searching a database table for a matching entry. Upon successful validation, the user gains access to the bowling shot analysis and performance improvement system and the application running on mobile device 104 displays the Welcome screen 500, shown in FIG. 5. After successful user login, Welcome screen 500 displays the user's first name 501 in the header as positive confirmation that the user successfully logged in. Welcome screen 500 then serves as the main menu for the mobile application, providing option buttons for capturing and analyzing bowling shot sensor data by an instruction to start bowling 502, followed by the functions of viewing historical game data 503, viewing historical shot data 504, entering or changing bowler profile information 505, viewing instructional media 506, and viewing miscellaneous information about the company 507.

Figure 5:
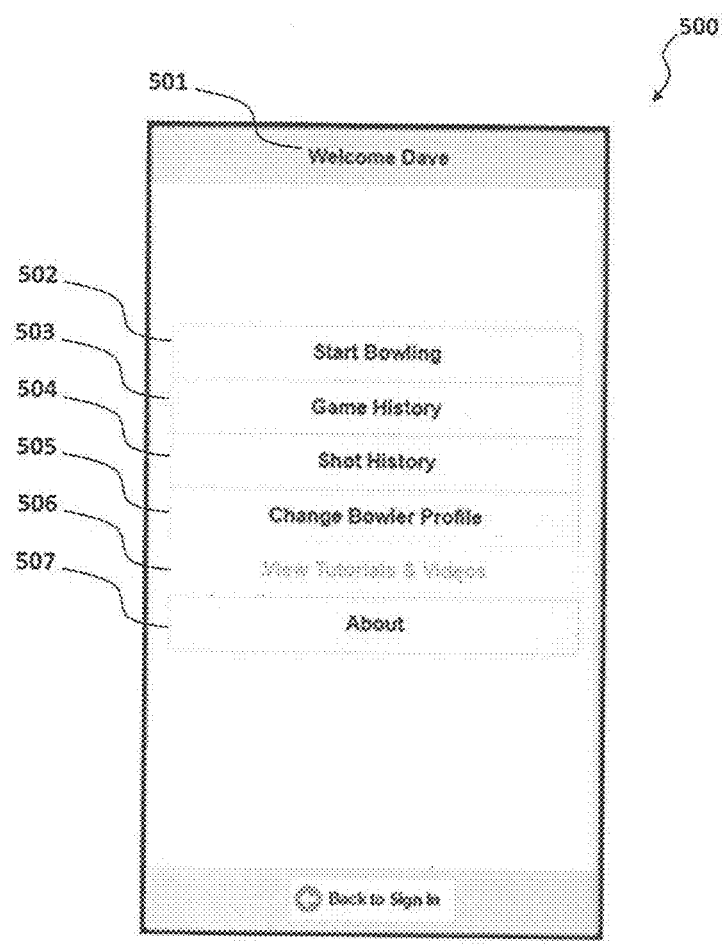
FIG. 5 shows the user Welcome screen 500 for the application running on a mobile device.
Figure 6:
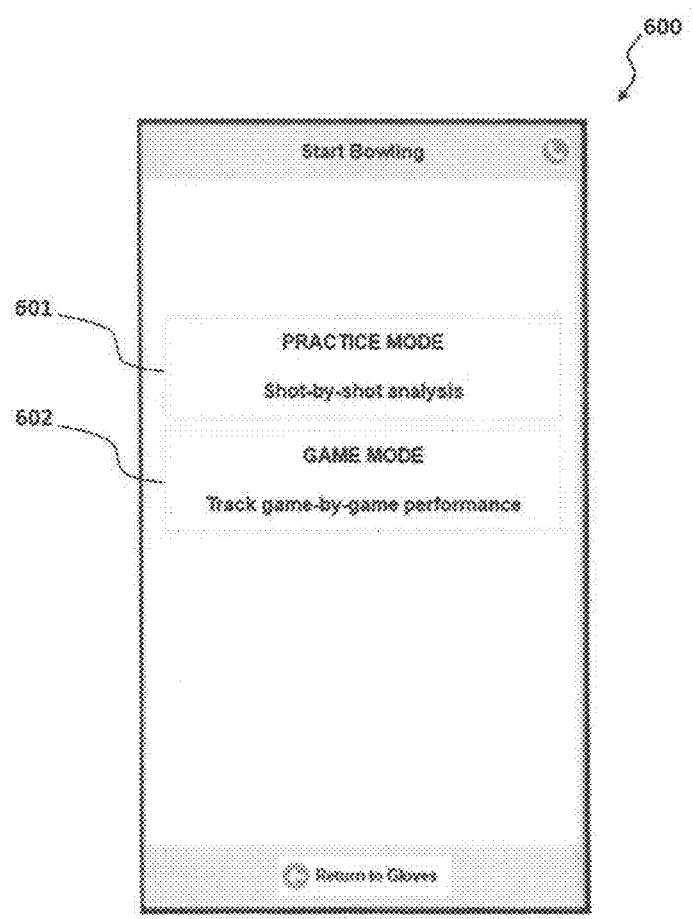
FIG. 6 shows the bowling Mode Selection screen 600 for the application running on a mobile device.

By touching the Start Bowling button 502 of mobile application screen 500 shown in FIG. 5, the Mode Selection screen 600 for the application running on the mobile device 104 appears, as shown in FIG. 6. Mode Selection screen 600 presents the user with two choices, selected by touching one of the buttons provided for Practice Mode 601 or Game Mode 602. Practice Mode 601 allows the bowler to freely take as many shots as desired during a practice session. The motion sensor device 101 automatically detects when a shot is taken and transmits the raw motion sensor data to the application running on the mobile device 104, whereby the mobile application calculates and displays the shot metrics, such as shown in the screen of FIG. 7.

Figure 7:
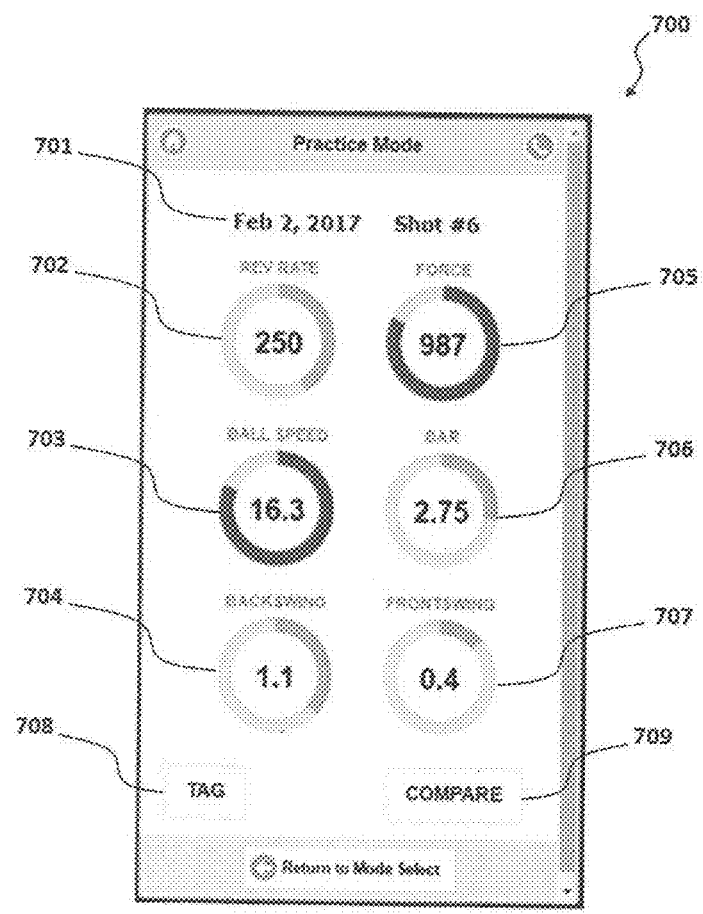
FIG. 7 shows the Practice Mode bowling shot analysis screen 700 for the application running on a mobile device.

FIG. 7 shows the Practice Mode bowling shot sensor data analysis screen 700 for the application running on the mobile device 104 appearing immediately after the user takes a shot. The mobile application timestamps and assigns a unique ID 701 to each shot, which are displayed at the top of analysis screen 700. Separate gauge-style readouts are provided for each of the calculated shot metrics, including ball revolution rate at release 702, ball speed at release 703, shot force at release 705, backswing duration 704, frontswing duration 707, and Bowler Armswing ration (BAR) 706. BAR is also herein referred to as Shot Tempo. When the bowler makes what he considers to be a great shot, the mobile application allows the user to "tag" the shot for comparison to future shots taken, with the goal of developing consistency for different types of shots (e.g. strike, 10-pin, 7-pin, etc.). The user is provided with TAG 708 and COMPARE 709 buttons for this purpose.

Figure 8:
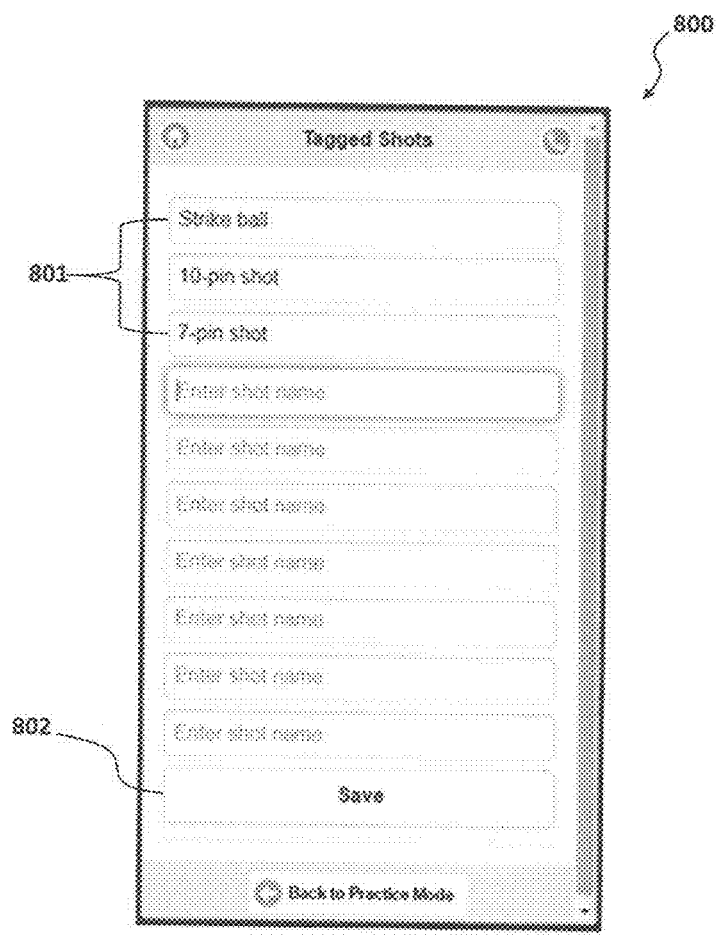
FIG. 8 shows the Tagged Shots screen 800 for the application running on a mobile device.

FIG. 8 shows the Tagged Shots screen 800 for the application running on the mobile device 104. Tagged Shots screen 800 appears immediately after the user touches the TAG button 708 on the Practice Mode bowling shot analysis screen 700 shown in FIG. 7. The mobile application allows the user to tag and store up to ten different shots. The Shot Name and associated metrics of a tagged shot are stored in the database on the Web Server 106. When Tagged Shots screen 800 is displayed, it is populated with previously-stored Tagged Shots 801. The user can freely edit existing Tagged Shots 801 and enter new ones by touching an empty button. All Tagged Shot entries shown on Tagged Shots screen 800 are stored in the database on Web Server 106 when the user touches the Save button 802.

When the user touches the Compare button 709 on the Practice Mode bowling shot analysis screen 700, shown in FIG. 7, the Compare Shot screen 900 for the application running on the mobile device 104 immediately appears. The Compare method allows the user to compare the metrics of the last bowling shot taken to those of a previously tagged bowling shot. Compare Shot screen 900 presents the date and shot ID of the last bowling shot taken and a radio button 901 corresponding to each Tagged Shot previously stored on Web Server 106. The user touches one button 901 corresponding to the specific Tagged Shot to which he wishes to compare his last shot taken. Pressing the OK button 902 will trigger the Compare Shot method of the mobile application to execute, which generates the screen of FIG. 10 on the mobile device 104.

Figure 9:
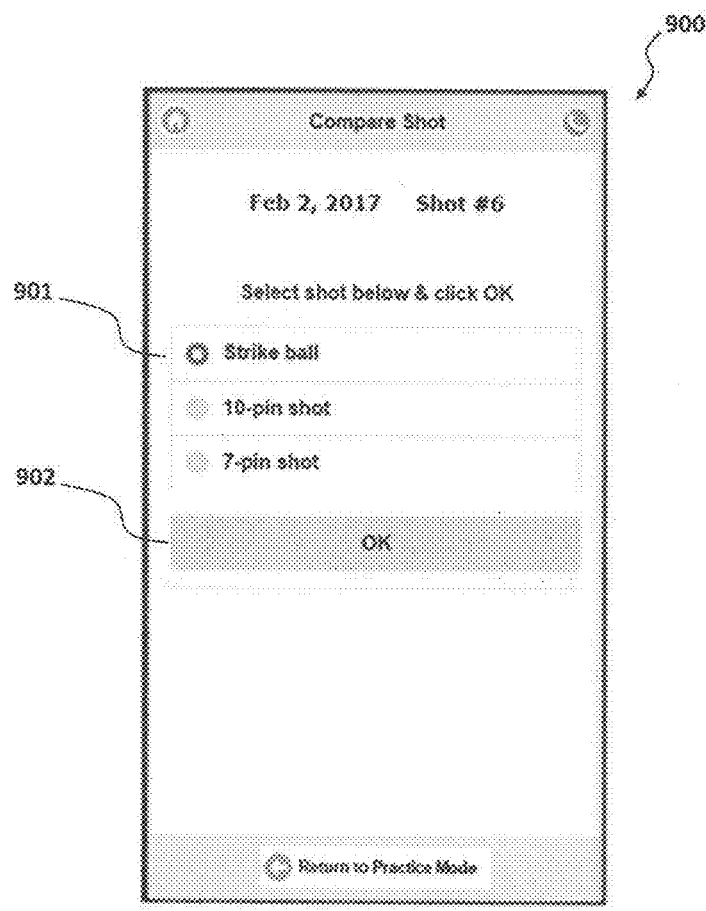
FIG. 9 shows the Compare Shot screen 900 for the application running on a mobile device.
Figure 10:
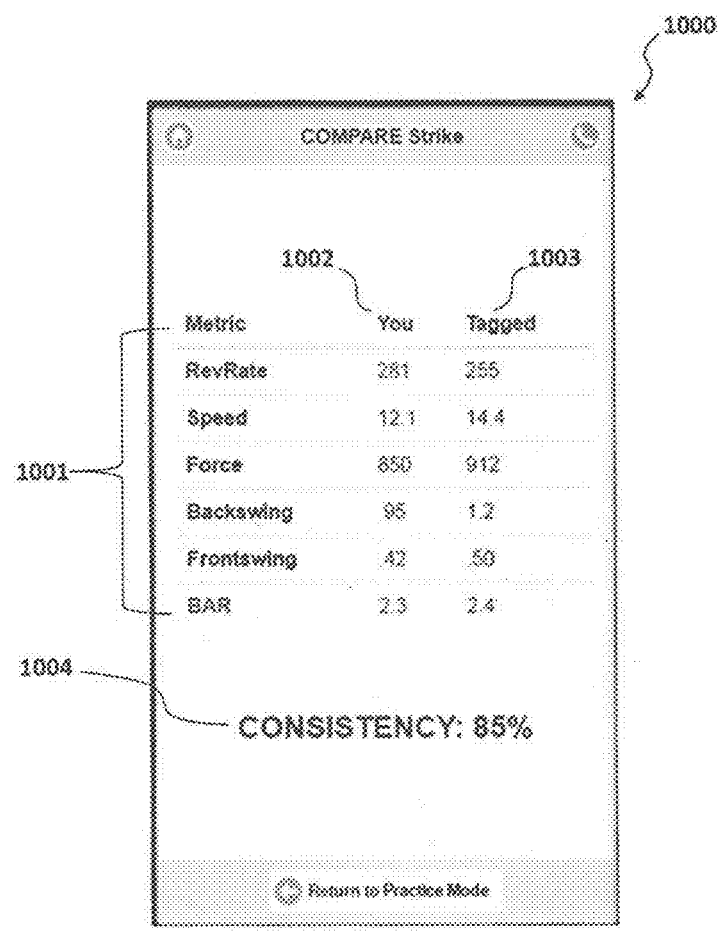
FIG. 10 shows the shot comparison metrics screen 1000 for the application running on a mobile device.
Figure 11:
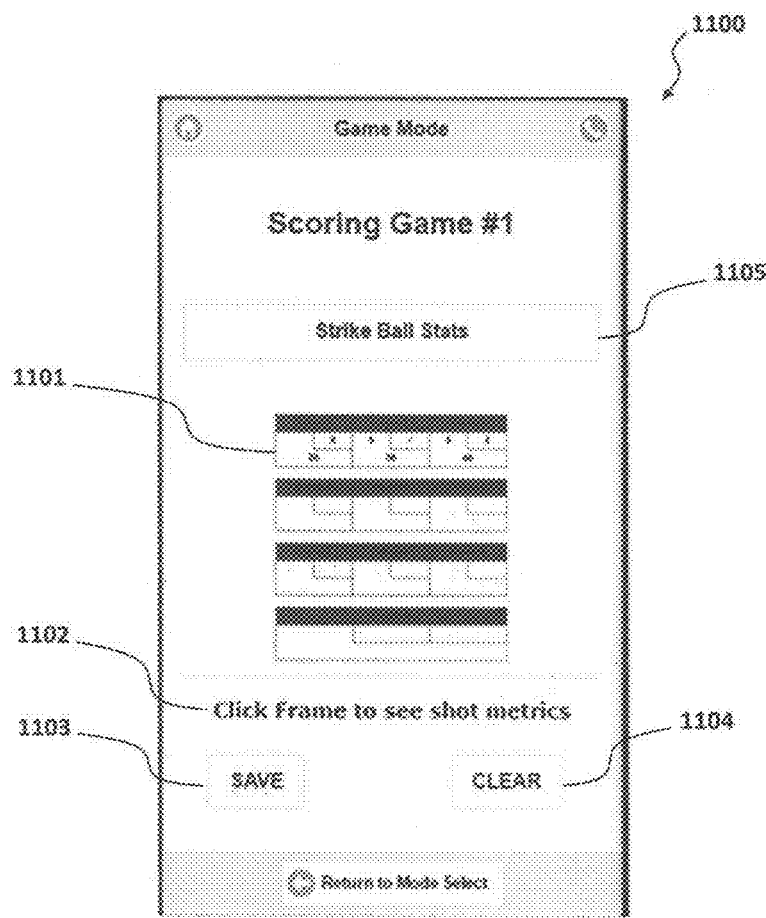
FIG. 11 shows the Game Mode scoresheet screen 1100 for the application running on a mobile device.

FIG. 10 shows the shot comparison metrics screen 1000 for the application running on the mobile device 104, which appears immediately after the user touches the OK button 902 on Compare Shot screen 900 shown in FIG. 9. The header the shot comparison metrics screen 1000 indicates the Tagged Shot being compared (in this case a Strike ball). Metrics screen 1000 displays two columns of metrics 1001; one with values for the last shot taken 1002 and one with values for Tagged Shot 1003 stored in the Web Server database 106. The Compare Shot method of the mobile application also calculates and displays an overall Consistency Rating 1004 as a percentage, calculated as:

$$\text{Consistency Rating} = 1 - \frac{1}{6}\sum_{i=1}^{6}\left|\left(\frac{(User_i - Tagged_i)}{Tagged_i} \times 100\%\right)\right| \quad (7)$$

where:
  $User_i = i_{th}$ metric for user's shot
  $Tagged_i = i_{th}$ metric for tagged shot After the user touches Game Mode button 602 on Mode Selection screen 600 shown in FIG. 6, Game Mode scoresheet screen 1100 appears on mobile device 104. FIG. 11. Game Mode 602 allows the user to record his game scores, frame-by-frame and shot-by-shot, on a bowling scoresheet as part of the mobile application. In Game Mode, all shot metrics are recorded in a database on the Web Server 106 for future analysis of performance metrics and shot consistency. Game Mode scoresheet screen 1100 shows the game number currently being scored at the top. The user enters his score for each shot by clicking on the highlighted frame on the scoresheet 1101. Scoresheet 1101 works similarly to a typical scoring system in a bowling alley, including marking strikes with an "X" symbol and spares with the "/" symbol for the second shot of any frame. By touching the "Click Frame to see shot metrics" button 1102, the mobile application displays the corresponding metrics for the last shot taken, similar to the screen depicted in FIG. 7. The user is able to TAG 708 and COMPARE 709 shots in Game Mode in the same manner as previously described for the Practice Mode shot screen 700. When the game is over, the user can touch SAVE button 1103 to store all game results in the database on Web Server 106, including metrics for all shots taken in the game. In this case, the mobile application automatically clears all frame scores in scoresheet 1101 and displays the next sequential game number at the top of screen 1100. The user can continue playing and scoring as many games as desired while in Game Mode. The user can also start a game over for any reason by touching CLEAR button 1104. In this case, the mobile application clears out the scores from scoresheet and is ready to accept new score entries. The displayed game number remains the same as it was before the user touched CLEAR 1104. At any time during Game Mode bowling, the user can touch the "Strike Ball Stats" button 1105 to check the consistency of his first ball shots taken so far in the game. The action causes the mobile application to compute the averages for all first ball metrics at that point in the game, as well as a Consistency Rating (CR) for each metric.

Figure 12:
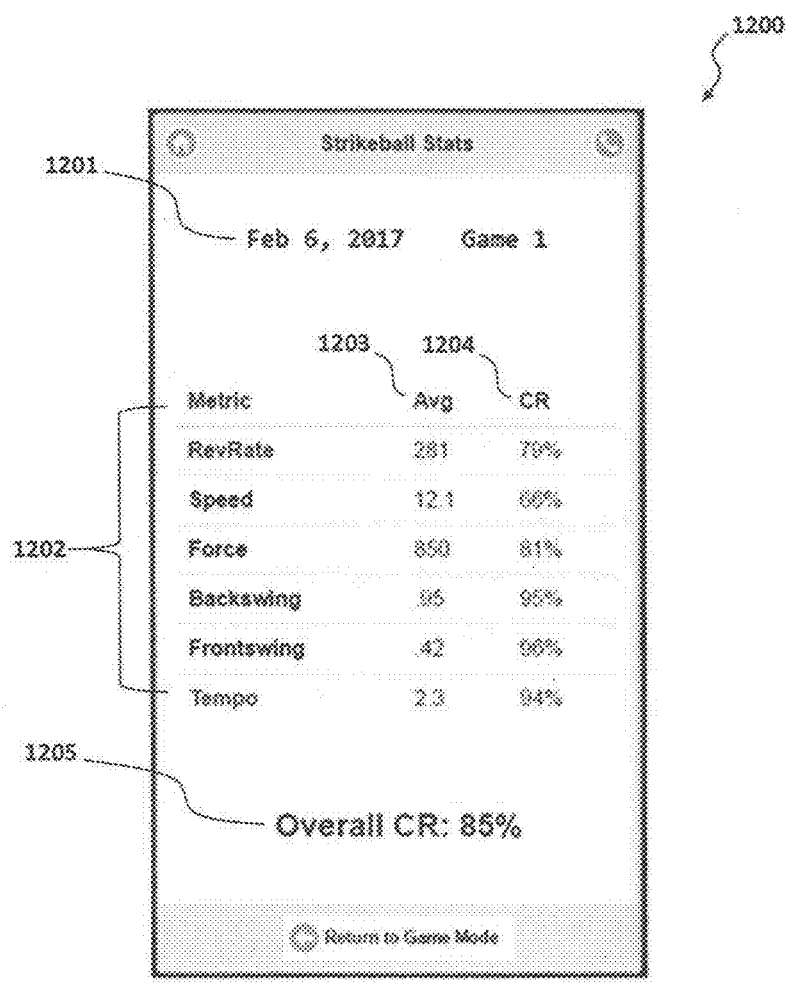
FIG. 12 shows the Strikeball Statistics screen 1200 for the application running on a mobile device.

FIG. 12 shows the Strikeball Stats screen 1200 for the application running on the mobile device 104 that appears when the user touches the "Strike Ball Stats" button 1105 in the Game Mode scoresheet screen 1100 shown in FIG. 11. The Game Date and Game Number are displayed at the top of the screen 1201. When this screen is entered, the mobile application computes and displays the averages of all first ball metrics 1203 at that point in the game, as well as an individual Consistency Rating ("CR") for each metric 1204.

The CR displayed for each metric 1204 is based on a statistical measure of variation across all first ball shots in the game. The mobile application computes CR from the Coefficient of Variation (CV) as follows:

$$CR_i = 1 - CV_i \quad (8)$$

where:

$$CV_i = \frac{\delta_i}{\mu_i}$$

$\delta_i$ = standard deviation of $i_{th}$ metric across the game
  $\mu_i$ = mean of $i_{th}$ metric across the game In addition to the individual CR's for each metric, the mobile application also computes an Overall Consistency Rating. The Overall CR 1205 displayed by the mobile application on the Strikeball Stats screen 1200 is simply the average of the six individual metric CR's from EQ. 8.

Figure 13:
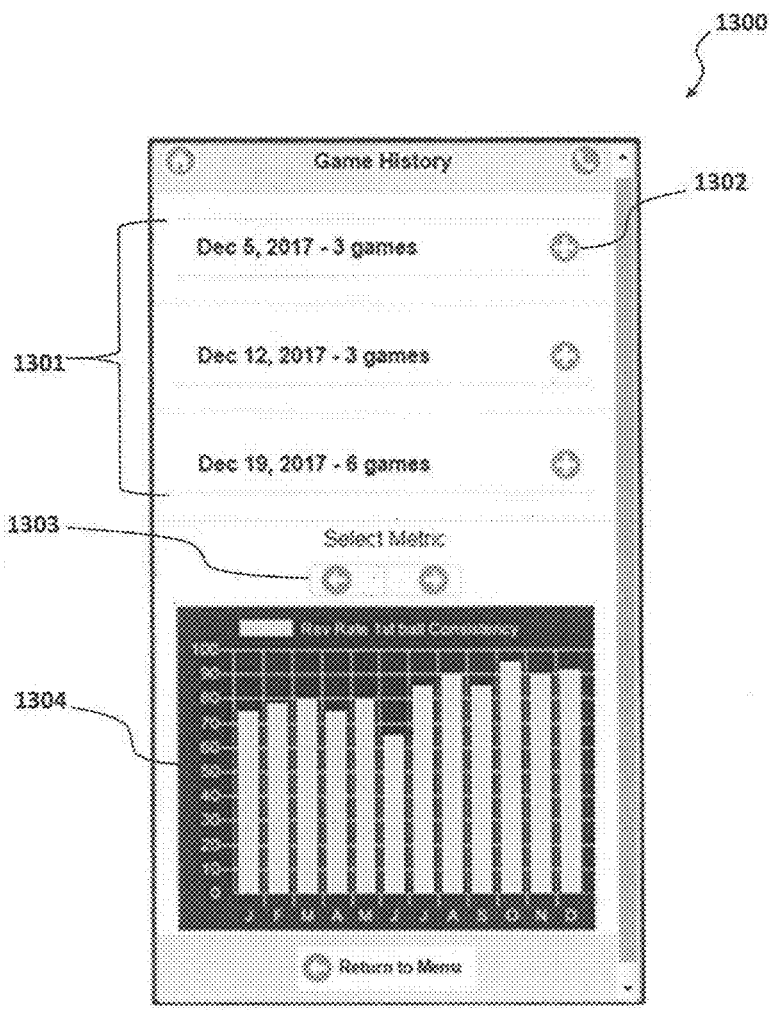
FIG. 13 shows the Game History screen 1300 for the application running on a mobile device.

FIG. 13 shows the Game History screen 1300 for the application running on the mobile device 104 that appears when the user touches the "Game History" button 503 in the Welcome screen 500 shown in FIG. 5. The Game History feature allows the user to view his recorded game scores and shot metrics, including shot consistency ratings. This screen shows all historical games 1301 recorded by the user, listed by expandable buttons that show the game date and the number of games played 1302. In addition, at the bottom of the screen is a graph of the user's consistency rating for a given metric 1304, with Rev Rate being the initial default selection. The graph displays the average monthly Consistency Ratings for the selected metric across the year. The user is provided with "Select Metric" left/right arrow buttons 1303 above the graph to allow selection of a different metric for the Consistency Rating graph 1304. When the user touches one of the expandable buttons 1302 for any date, the mobile application presents a list of recorded games, allowing the user to select any one game and drill down into the recorded data for that game. The mobile application displays the selected game data in a bowling scoresheet display.

Figure 14:
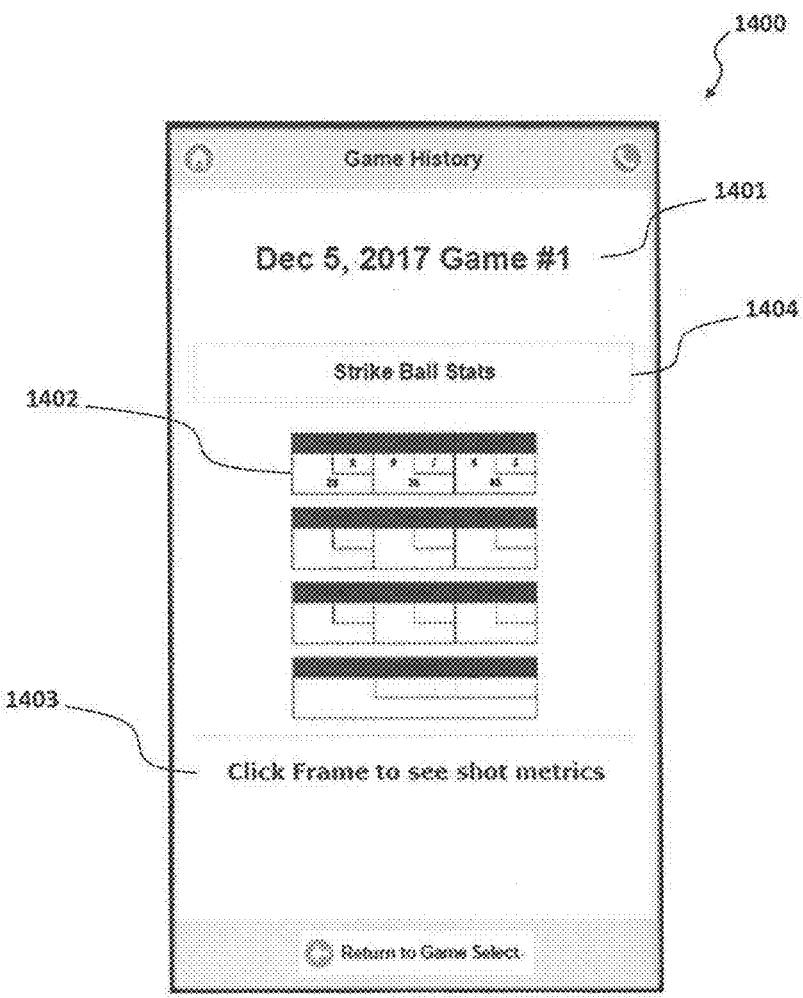
FIG. 14 shows the Game History scoresheet screen 1400 for the application running on a mobile device.

FIG. 14 shows the Game History scoresheet screen 1400 for the application running on the mobile device 104 that appears when the user drills down into one specific game from the Game History screen 1300 shown in FIG. 13. The Game Date and Game Number 1401 are displayed at the top of the screen 1400. this scoresheet 1402 has similar features as the scoresheet previously described for Game Mode in FIG. 11, including viewing shot metrics for any frame 1403 and Strike Ball Stats 1404.

Figure 15:
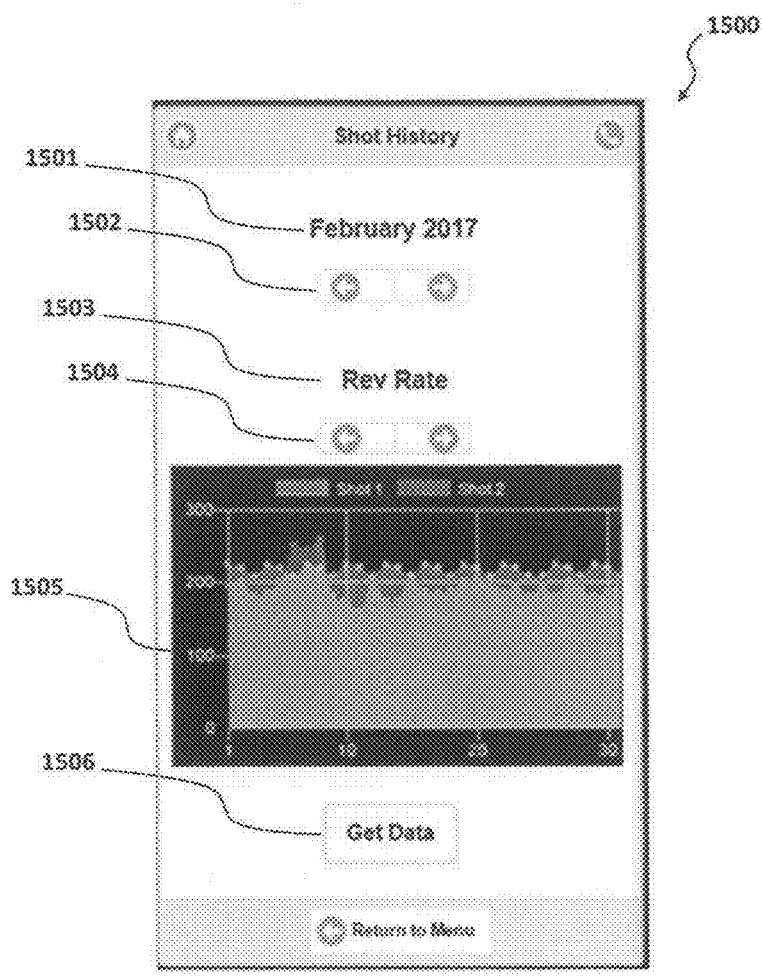
FIG. 15 shows the Shot History screen 1500 for the application running on a mobile device.

FIG. 15 shows the Shot History screen 1500 for the application running on the mobile device 104 that appears when the user touches the "Shot History" button 504 in the Welcome screen 500 shown in FIG. 5. The Shot History feature allows the user to view his recorded shot metrics across monthly game play. By default, the mobile application reads all recorded shot data from the Web Server 106 and displays the most recent month's of Rev Rate data on the graph 1505. Control buttons are provided that allow the user to select a different date 1502 and a different metric 1504 for display. The Get Data button 1506 must be touched to retrieve new data from the Web Server 106. The selected date 1501 and selected metric 1503 are shown on the display screen 1500. The graph 1505 includes a plot for both the first and second shots. The first and second shot plots are time-aligned, meaning that they correspond to the same game and frame. Note that there will be no second shots for frames that the user strikes on his first shot, causing gaps in the plot for the second shot (not shown in FIG. 15).

While the ideas herein disclosed have been described by means of specific embodiments and applications thereof, numerous modifications and variations could be made thereto by those skilled in the art without departing from the scope of the invention set forth in the claims.

What is claimed:

1. A system for improving bowling shot performance, comprising:
    a bowling motion sensor device, wearable by a user, for obtaining bowling shot data, said bowling motion sensor comprising; sensors for detecting bowling shot motions, an integrated sensor/computing platform configured to recognize a bowling shot while it is being made by using the steps comprising,
        i. capturing said bowling shot data generated by said bowling motion sensor device for said bowling shot, said bowling shot data comprising accelerometer data and gyroscope data,
        ii. calculating magnitudes for said accelerometer and gyroscope data,
        iii. measuring a time duration of said bowling shot from initiation of a bowler's backswing, front swing and point of ball release,
        iv. determining a backswing start time of said bowling shot as measured from the point of ball release, and
        v. determining whether said point of ball release coincides with a maximum magnitude of said gyroscope data, and whether a time duration of said backswing as measured from said point of ball release coincides with a bowling shot recognition pattern,
    said integrated sensor/computing platform being further configured to capture said bowling shot data generated by said bowling shot if a bowling shot is recognized and to wirelessly transmit said bowling shot data;
    a mobile device for wirelessly receiving said bowling shot data transmitted from said bowling motion sensor device, said mobile device comprising; a microcomputer system configured to wirelessly receive said bowling shot data, and to further wirelessly transmit said bowling shot data, and said mobile device further having a touch-capable user interface display;
    an Internet-connected Web server computer; said Web server computer configured to wirelessly receive and store said bowling shot data transmitted from said mobile device, to calculate bowling shot metrics from said received bowling shot data, and to wirelessly communicate said calculated bowling shot metrics back to said mobile device for display to the user;
    whereby said user adjusts a bowling shot in accordance with the bowling shot metrics displayed on said mobile device.

2. The system of claim 1, wherein said bowling motion sensor further comprises a glove, a wristband, an armband, a compression sleeve, and other types of apparel worn on the body.

3. The system of claim 1, wherein said bowling motion sensor device further comprises a motion sensor microcomputer system comprising a memory, said memory configured to continuously acquire bowling shot data, perform data processing operations on said bowling shot sensor data, and to periodically and wirelessly communicate said acquired bowling shot data to said mobile device for further processing.

4. The system of claim 1, wherein said mobile device comprises a smart phone or tablet computer; said smart phone or tablet computer comprising operating system software (iOS or Android), Wi-Fi wireless data connectivity, cellular wireless data connectivity, Bluetooth wireless data connectivity, touch-sensitive user interface display, and Internet browser software.

5. The system of claim 1, wherein said mobile device displays said bowling shot metrics after each bowling shot.

6. The system for improving bowling shot performance of claim 1 further comprising an Internet-connected analytic server, said analytic server being configured to receive said bowling shot data from said Web server through one or more Application Programming Interfaces (APIs), calculate bowling shot metrics from said bowling shot data, and to communicate said bowling shot metrics back to said Web server, which subsequently communicates said bowling shot metrics back to said mobile device for display to the user.

7. The system for improving bowling shot performance of claim 1, wherein said bowling motion sensor comprises digital accelerometer sensors, digital gyroscope sensors, and digital magnetometer sensors.

8. The system for improving bowling shot performance of claim 1, wherein said integrated sensor/computing platform is further configured to capture body motion data from said bowling motion sensor.

9. The system for improving bowling shot performance of claim 8, wherein said calculated bowling shot metrics include estimated ball revolutions rate at ball release, ball speed at ball release, ball force at ball release, bowling shot backswing duration, bowling shot front swing duration and bowling shot tempo.

10. The system of claim 1, wherein said calculated bowling shot metrics include; ball revolution rate at ball release, ball speed at ball release, ball force at ball release, said duration time of said bowling shot backswing, duration time of said bowling shot front swing and bowling shot tempo.

11. The system of claim 10, wherein said calculated bowling shot metrics further comprise a bowler arm-swing ratio, said arm-swing ratio calculated as said duration time of said bowling shot backswing divided by said duration time of said bowling shot front swing.

12. The system of claim 10, further comprising calculating and displaying a numerical consistency rating between said bowling metrics of said current bowling shot and said bowling metrics of a previously designated successful bowling shot.

13. A method for improving bowling shot performance, said method comprising the steps of:
   taking bowling shots with a bowling ball in either bowling practice or a game of bowling, by a user;
   using a wearable bowling motion sensor device comprising sensors for detecting bowling shot motions and an integrated sensor/computing platform configured to recognize a bowling shot while it is being made;
   recognizing that a bowling shot is being made by;
      i. capturing bowling shot data generated by said bowling motion sensor device for said bowling shot, said bowling shot data comprising accelerometer data and gyroscope data,
      ii. calculating magnitudes for said accelerometer and gyroscope data,
      iii. measuring a time duration of said bowling shot from initiation of a bowler's backswing, front swing and point of ball release,
      iv. determining a backswing start time of said bowling shot as measured from the point of ball release, and
      v. determining whether said point of ball release coincides with a maximum magnitude of said gyroscope data, and whether the time duration of said backswing as measured from said point of ball release coincides with a bowling shot recognition pattern;
   if a bowling shot is recognized, wirelessly transmitting said bowling shot data from said bowling motion sensor to a mobile device, said mobile device comprising a microcomputer system configured to wirelessly receive said bowling shot data, and to further wirelessly transmit said bowling shot data; said mobile device further comprising a touch-capable user interface display;
   transmitting said bowling shot data from said mobile device to an Internet-connected Web server computer; said Web server computer configured to wirelessly receive said bowling shot data;
   using said Web server computer; storing said bowling shot data transmitted from said mobile device, calculating bowling shot metrics from said received bowling shot data, and wirelessly communicating said calculated bowling shot metrics back to said mobile device for display to the user;
   displaying said bowling shot metrics on said mobile device;
   designating which of said bowling shots were successful bowling shots, and which of said bowling shots is a current bowling shot;
   storing said bowling shot metrics for specific designated successful bowling shots;
   comparing said bowling shot metrics from said current shot with said bowling shot metrics from said designated stored bowling shot metrics; and
   said user adjusting the metrics of a subsequent bowling shot to conform with said bowling shot metrics of said designated successful bowling shots displayed on said mobile device.

14. The method for improving bowling shot performance of claim 13, wherein said bowling shot metrics include; ball revolution rate at ball release, ball speed at ball release, ball force at ball release, duration time of said bowling shot backswing, duration time of said bowling shot front swing and bowling shot tempo.

15. The method of claim 14, wherein said calculated bowling shot metrics further comprise a bowler arm-swing ratio. said arm-swing ratio calculated as said duration time of said backswing divided by said duration time of said front swing.

16. The method of claim 15, further comprising displaying said bowling shot metrics on said mobile device after each bowling shot.

17. The method of claim 15, further comprising calculating and displaying a numerical consistency rating between said bowling metrics of said current bowling shot and said bowling metrics of a previously designated successful bowling shot.

18. The method of claim 15, further comprising the steps of recording bowling game scores and displaying on said mobile device; average scores of a first-thrown ball in a frame across all frames in a game, individual consistency ratings for each bowling shot metric based on statistical variance across said game, and an average consistency rating across all bowling shot metrics.

19. The method of claim 15, further comprising the steps of recording historical game information, comprising game scores, bowling shot metrics, and bowling shot consistency ratings, in a database on said Internet-connected Web server computer, and displaying said historical game information on said mobile device.

20. The method of claim 19, further comprising the steps of recording historical bowling shot information, comprising bowling shot metrics for a first bowling shot and a second bowling shot in each frame across monthly game play in said database on said Internet-connected Web server computer, and displaying said historical bowling shot information on said mobile device.

* * * * *